US008557580B2

(12) United States Patent (10) Patent No.: US 8,557,580 B2
Daigh et al. (45) Date of Patent: Oct. 15, 2013

(54) METHODS AND COMPOSITIONS FOR THE DIFFERENTIATION OF STEM CELLS

(75) Inventors: Christine Daigh, Middleton, WI (US); Peter Fuhrken, Madison, WI (US); Giorgia Salvagiotto, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 454 days.

(21) Appl. No.: 12/709,764

(22) Filed: Feb. 22, 2010

(65) Prior Publication Data

US 2010/0216181 A1 Aug. 26, 2010

Related U.S. Application Data

(60) Provisional application No. 61/154,210, filed on Feb. 20, 2009.

(51) Int. Cl.
*C12N 5/00* (2006.01)
*C12N 5/02* (2006.01)
*C12N 5/078* (2010.01)

(52) U.S. Cl.
USPC .......................................... 435/377; 435/325

(58) Field of Classification Search
None
See application file for complete search history.

(56) References Cited

U.S. PATENT DOCUMENTS

| | | | |
|---|---|---|---|
| 7,442,548 B2 | 10/2008 | Thomson et al. | 435/377 |
| 7,449,334 B2 | 11/2008 | Thomson et al. | 435/366 |
| 7,781,214 B2 | 8/2010 | Smith et al. | 435/377 |
| 7,892,830 B2 * | 2/2011 | Bergendahl et al. | 435/384 |
| 8,211,697 B2 * | 7/2012 | Sakurada et al. | 435/377 |

FOREIGN PATENT DOCUMENTS

| | | |
|---|---|---|
| WO | WO 2006/050330 | 5/2006 |
| WO | WO 2009/135206 | 11/2009 |

OTHER PUBLICATIONS

Ferreira et al., Biomaterials. Jun. 2007;28(17):2706-2717.*
Gerecht-Nir et al., Lab Invest 2003, 83:1811-1820.*
Watanabe et al., 2007, Nature Biotechnology, 25: 681-686.*
Bai et al., "Sequential roles of BMP-4, VEGF and FGF-2 in generation of CD34+ vascular progenitor cells from human embryonic stem cells under animal product-free condition," *Cell Research*, 18:s108, 2008.
Kennedy et al., "Development of the hemangioblast defines the onset of hematopoiesis in human ES cell differentiation cultures," *Blood*, 109(7)::2679-2687, 2007.
Lu et al., "Robust generation of hemangioblastic progenitors from human embryonic stem cells," *Regen. Med.*, 3(5):693-704, 2008.
Millman et al., "The effects of low oxygen on self-renewal and differentiation of embryonic stem cells," *Curr. Opin. Organ Transplant*, 14:694-700, 2009.

PCT International Search Report and Written Opinion, issued in International Patent Application No. PCT/US2010/024881, dated Aug. 6, 2010.
Pearson et al., "The stepwise specification of embryonic stem cells to hematopoietic fate is driven by sequential exposure to Bmp4, activin A, bFGF and VEGF," *Development*, 135:1525-1535, 2008.
Pick et al., "Differentiation of human embryonic stem cells in serum-free medium reveals distinct roles for bone morphogenetic protein 4, vascular endothelial growth factor, stem cell factor, and fibroblast growth factor 2 in hematopoiesis," *Stem Cells*, 25:2206-2214, 2007.
Wang, "BMP4 and TGFbeta differentially regulate CD34+ progenitor development in human embryonic stem cells through SMAD-dependent pathway," *Blood (ASH Annual Meeting Absracts)*, 112: Abstract 889, 2008.
Amit et al., "Feeder layer- and serum-free culture of human embryonic stem cells," *Biology of Reproduction*, 70: 837-845, 2004.
Bashey et al., "Peripheral blood progenitor cell mobilization with intermediate-dose cyclophosphamide, sequential granulocyte-macrophage-colony-stimulating factor and granulocyte-colony-stimulating factor, and scheduled commencement of leukapheresis in 225 patients undergoing autologous transplantation," *Transfusion*, 47 (11): 2153-2160, 2007.
Bhardwaj et al., "Sonic hedgehog induces the proliferation of primitive human hematopoietic cells via BMP regulation," *Nat. Immunol.*, 2: 172-180, 2001.
Bhatia et al., "Bone Morphogenetic Proteins Regulate the Developmental Program of Human Hematopoietic Stem Cells," *J. Exp Med.*, 189: 1139-1148, 1999.
Chadwick et al., "Cytokines and BMP-4 promote hematopoietic differentiation of human embryonic stem cells," *Blood.*, 102 (3): 906-915, 2003.
Cipolleschi et al., "The role of hypoxia in the maintenance of hematopoietic stem cells," *Blood.*, 82 (7): 2031-2037, 1993.
Davison and Zon, "Turning mesoderm into blood: the formation of hematopoietic stem cells during embryogenesis," *Curr. Top Dev. Biol.*, 50: 45-60, 2000.
Ezashi et al., "Low O2 tensions and the prevention of differentiation of hES cells," *Proc. Natl. Acad. Sci. USA*, 102 (13): 4783-4788, 2005.
Fadilah et al., "Cord Blood CD34+ Cells Cultured with FLT3L, Stem Cell Factor, Interleukin-6, and IL-3 Produce $CD11c^+CD1a^-c^-$ Myeloid Dendritic Cells," *Stem Cells Dev.*, 16 (5): 849-856, 2007.
Forsythe et al., "Activation of vascular endothelial growth factor gene transcription by hypoxia-inducible factor 1," *Mol. Cell. Biol.*, 16 (9): 4604-4613, 1996.

(Continued)

*Primary Examiner* — Daniel C Gamett
(74) *Attorney, Agent, or Firm* — Parker Highlander PLLC

(57) ABSTRACT

The present invention provides methods and compositions for the production of hematopoietic progenitor cells or endothelial progenitor cells from human pluripotent stem cells using a defined cell culture medium without the need to utilize feeder cells or serum. In some embodiments, differentiation is accomplished using hypoxic atmospheric conditions. The defined medium of the present invention may contain growth factors and a matrix component. The hematopoietic progenitor cells may be further differentiated into cell lineages including red blood cells, macrophages, granulocytes, and megakaryocytes. The endothelial progenitor cells may be further differentiated into endothelial cells. Also disclosed are screening assays for identification of candidate substances that affect differentiation of pluripotent stem cells into progenitor cells.

36 Claims, No Drawings

(56) References Cited

OTHER PUBLICATIONS

Harrison et al., "Oxygen saturation in the bone marrow of healthy volunteers," *Blood.*, 99 (1): 394, 2002.

Huber et al., "Cooperative effects of growth factors involved in the induction of hematopoietic mesoderm," *Blood.*, 92 (11): 4128-4137, 1998.

Kadaja-Saarepuu et al., "CD43 promotes cell growth and helps to evade FAS-mediated apoptosis in non-hematopoietic cancer cells lacking the tumor suppressors p53 or ARF," *Oncogene.*, 27 (12): 1705-1715, 2008.

Kaufman et al., "Hematopoietic colony-forming cells derived from human embryonic stem cells," *Proc. Natl. Acad. Sci. USA*, 98 (1,9): 10716-10721, 2001.

Ludwig et al., "Derivation of human embryonic stem cells in defined conditions," *Nature Biotech.*, 2: 185-187, 2006.

Ludwig et al., "Feeder-independent culture of human embryonic stem cells," *Nature Methods*, 3 (8): 637-646, 2006.

Ma et al., "Novel method for efficient production of multipotential hematopoietic progenitors from human embryonic stem cells," *Int. J. Hematol.*, 85 (5): 371-379, 2007.

Marshall et al., "Polarized expression of bone morphogenetic protein-4 in the human aorta-gonad-mesonephros region.," *Blood*, 96 (4): 1591-1593, 2000.

Nakagawa et al., "Generation of induced pluripotent stem cells without Myc from mouse and human fibroblasts," *Nat. Biotechnol.*, 26 (1): 101-106, 2008.

Ramirez-Bergeron et al., "Hypoxia affects mesoderm and enhances hemangioblast specification during early development.," *Development*, 131 (18): 4623-4634, 2004.

Ratajczak et al., "Effect of basic (FGF-2) and acidic (FGF-1) fibroblast growth factors on early haemopoietic cell development," *Br. J Haematol.*, 93 (4): 772-782, 1996.

Slukvin et al., In: *Directed Production of Sepcific Blood Lineages from Human Embryonic Stem Cells*, #33, ASCI/AAP Joint Meet. Posters, 2007.

Takahashi et al., "Induction of pluripotent stem cells from adult human fibroblasts by defined factors," *Cell*, 131 (5): 861-872, 2007.

Takahashi et al., "Induction of pluripotent stem cells from fibroblast cultures," *Natl. Protoc.*, 2 (12): 3081-3089, 2007.

Vodyanik et al., "Leukosialin (CD43) defines hematopoietic progenitors in human embryonic stem cell differentiation cultures," *Blood*, 108 (6): 2095-2105, s2006.

Wang et al., "Endothelial cells derived from human embryonic stem cells form durable blood vessels in vivo," *Nature Biotechnology*, 25 (3): 317-318, 2007.

Yamazaki et al., "Potential of dental mesenchymal cells in developing teeth," *Stem Cells*, 25 (1): 78-87, 2007.

Yu et al., "Induced pluripotent stem cell lines derived from human somatic cells," *Science*, 318 (5858): 1917-1920, 2007.

\* cited by examiner

METHODS AND COMPOSITIONS FOR THE DIFFERENTIATION OF STEM CELLS

This application claims priority to U.S. Provisional Patent Application Ser. No. 61/154,210, filed on Feb. 20, 2009, which is hereby incorporated by reference.

BACKGROUND OF THE INVENTION

1. Field of the Invention

The present invention relates generally to the fields of molecular biology and medicine. More particularly, it concerns methods and compositions for the production of progenitor cells, such as hematopoietic progenitor cells and endothelial progenitor cells from embryonic stem cells. The invention also relates to kits for the production of progenitor cells and methods of screening for substances that promote differentiation of pluripotent stem cells.

2. Description of Related Art

In vitro, human embryonic stem cells are capable of indefinite proliferation in culture and are thus capable, at least in principle, of supplying cells and tissues for the replacement of failing or defective human tissue. Due to the significant medical potential of hematopoietic stem and progenitor cells, substantial work has been done to try to improve methods for the differentiation of hematopoietic progenitor cells from embryonic stem cells. In the human adult, a small number of hematopoietic stem cells present primarily in bone marrow produce heterogeneous populations of actively dividing hematopoietic (CD34+) progenitor cells that differentiate into all the cells of the blood system. The CD34+ marker is an imprecise definition of hematopoietic cells since other cell types, notably endothelial cells (blood vessels), also express CD34. Thus, other markers, such as the CD43 marker, may also be used to help identify hematopoietic progenitor cells (e.g., Kadaja-Saarepuu et al., 2007; Vodyanik et al., 2006). In an adult human, hematopoietic progenitors proliferate and differentiate to generate hundreds of billions of mature blood cells daily. Hematopoietic progenitor cells are also present in cord blood.

In addition to hematopoietic cells, it is useful to differentiate endothelial progenitor cells, and ultimately endothelial cells, from embryonic stem cells. Endothelial cells comprise the lining of the blood vessels and are important for a variety of processes in the body. For example, endothelial cells play roles in angiogenesis, regulation of blood pressure, blood clotting, inflammation, and filtration. Endothelial cells are a heterogeneous group of cells and may have a variety of characteristics depending upon vessel size, specification to a specific organ, and morphology. Some characteristics of endothelial cells include expression of CD31, CD105 (endoglin), and Willebrand factor (also called Factor VIII), as well as the ability to take up acetylated low density lipoprotein (ac-LDL).

Previous methods to promote the differentiation of pluripotent stem cells (PSCs) have required the formation of embryoid bodies (e.g., Chadwick et al., 2003) or the use of mouse feeder cells such as mouse embryonic fibroblasts (e.g., Wang et al., 2007). Unfortunately, these approaches have several drawbacks that may limit their clinical potential.

The formation of "embryoid bodies" (EBs), or clusters of growing cells, to induce differentiation generally involves in vitro aggregation of human pluripotent stem cells into EBs and allows for the spontaneous and random differentiation of human pluripotent stem cells into multiple tissue types that represent endoderm, ectoderm, and mesoderm origins. These three-dimensional EBs contain some fraction of progenitor cells that may be used to produce hematopoietic cells and endothelial cells. Unfortunately, methods for the formation of EBs are often inefficient and laborious, and the multiple complex steps involved in the formation and dissociation of EBs can make use of automation more difficult. For example, the process for forming EBs is inefficient in that it usually requires an entire colony of hematopoietic progenitor cells. Further, utilizing EBs requires complex methods such as the dissociation of embryoid bodies, which presents substantial problems for automation or large-scale automation.

The culture of human pluripotent cells with feeder cell lines, such as mouse fibroblasts, presents the risk of unexpected transformations that have previously been associated with interspecies exposure during co-culture. Since one of the objectives of human pluripotent stem cell cultures is to create tissues which can ultimately be transplanted into a human body, it is highly desirable that the stem cells are not exposed to cells of another species or to a medium that has been used to culture cells of another species. Accordingly, defining a culture condition that will permit the differentiation of human pluripotent stem cells into the hematopoietic lineage or endothelial lineage without a co-culture step of any kind is of great interest in the continued development of techniques for the production of human hematopoietic progenitor cells or endothelial progenitor cells from human pluripotent stem cells.

Using serum in differentiation medium can also present certain drawbacks and limitations. Serum, e.g., as used in Chadwick et al. (2003), is an animal product that may be used to provide nutrients to growing cells. However, the composition of a particular serum is uncertain across different batches, meaning that one batch of serum may have different growth factors or different concentrations of growth factors as compared to a different batch of the same type of serum. These uncertainties may contribute to the variable yield of hematopoietic cells produced across experiments performed under the same conditions. Additionally, the use of serum may present substantial regulatory issues during clinical development, further complicating commercialization.

There currently exists a clear need for efficient methods of differentiating pluripotent stem cells into hematopoietic progenitor cells or endothelial progenitor cells without either exposing the cells to material from another animal species or forming embryoid bodies. Further, there exists a need for a defined differentiation medium and conditions that allow further differentiation steps, give reproducible results, and do not require inclusion of serum or feeder cells.

SUMMARY OF THE INVENTION

The present invention overcomes limitations in the prior art by providing methods and compositions for the production and reproducible differentiation of hematopoietic cells and endothelial cells from pluripotent stem cells without the need to use stromal feeder cells or form embryoid bodies. Moreover, methods of the invention promote improved pluripotent stem cell differentiation by, for example, using a defined differentiation medium and specific atmospheric conditions. As used herein, the terms "defined conditions," "defined medium," and "defined differentiation" refer to culture conditions, wherein the culture has known quantities of all ingredients and does not utilize undefined ingredients, serum, or feeder cells (e.g., mouse embryonic fibroblasts). An "undefined ingredient" is an ingredient that contains unknown components, or contains known components in unknown amounts. Defined conditions may be particularly useful, e.g., in applications where differentiated cells may be therapeutically administered to a subject, such as a human patient. The term "serum," as used herein, refers to a non-human animal product that may be added to a culture to provide nutrients to growing cells.

In some embodiments, the culture is essentially free of non-human animal proteins, non-human animal nucleic acids, or both. In other embodiments, the culture is essentially free of non-human mammalian proteins, non-human mammalian nucleic acids, or both.

In certain embodiments, the invention provides methods for differentiating a human pluripotent stem cell into a CD34+, CD31+, or CD43+ progenitor cell. Such methods may include a step wherein a pluripotent stem cell is cultured or differentiated in a medium that is free or essentially free of feeder cells and that comprises a matrix component and at least one recombinant growth factor, such as BMP-4, VEGF, or bFGF. The pluripotent stem cells may be differentiated under a hypoxic atmosphere having less than about 5.5% oxygen for a period of time to provide the CD34+, CD31+, or CD43+ progenitor cells.

As used herein, a "pluripotent cell" or "pluripotent stem cell" is a cell that has the capacity to differentiate into essentially any fetal or adult cell type. Exemplary types of pluripotent stem cells may include, but are not limited to, embryonic stem cells and induced pluripotent stem cells (or iPS cells). Such a pluripotent stem cell may be a mammalian pluripotent stem cell. In certain embodiments, the pluripotent stem cell is a human pluripotent stem cell.

In certain aspects, the invention provides methods and compositions for differentiating pluripotent stem cells into progenitor cells. A "progenitor cell," as used herein, refers to a lineage-committed cell derived from a pluripotent stem cell. Thus, progenitor cells are more differentiated than pluripotent stem cells, but still have the capacity to differentiate into more than one type of cell. For example, a hematopoietic progenitor cell is more differentiated than a pluripotent stem cell, but the hematopoietic progenitor cell still has the capacity to differentiate into, for example, an erythrocyte, a macrophage, a granulocyte, a megakaryocyte, a dendritic cell, or a mast cell. In some embodiments of the invention, the progenitor cell is a hematopoietic progenitor cell. In other embodiments, the progenitor cell is an endothelial progenitor cell. In yet other embodiments, the progenitor cell is a hematoendothelial (or hemangioblast) progenitor cell, which is capable of differentiating into hematopoietic cells or endothelial cells.

Some embodiments of the methods disclosed herein regard cells that express specific surface markers. For example, some methods are directed to cells, such as progenitor cells, that express CD34. Examples of CD34+ progenitor cells include, but are not limited to, hematopoietic progenitor cells, endothelial progenitor cells, and hematoendothelial progenitor cells. Other embodiments regard CD31+ progenitor cells, which may include, but are not limited to, endothelial progenitor cells and hematoendothelial progenitor cells. Some aspects of the invention regard CD43+ cells, which may include, but are not limited to, hematopoietic progenitor cells.

Certain embodiments of the invention regard methods for differentiating a pluripotent stem cell into a progenitor cell, including growing a pluripotent stem cell in a differentiation medium that contains at least one matrix component and at least one recombinant growth factor but is free or essentially free of feeder cells. Matrix components useful in methods and compositions of the invention may include, but are not limited to, fibronectin, collagen, or an RGD peptide. In particular embodiments, the culture contains one or more recombinant growth factors, meaning that the growth factors are produced using recombinant DNA technology. Growth factors useful in methods and compositions of the invention include, but are not limited to, BMP-4, VEGF, or bFGF. A culture medium of the invention may contain two or more recombinant growth factors. In certain embodiments, the culture medium contains VEGF and bFGF.

In some aspects, the invention is directed to a method for differentiating pluripotent stem cells, wherein the culture medium is free or essentially free of feeder cells. In other aspects, the invention is directed to a method for differentiating pluripotent stem cells, wherein the culture medium is free or essentially free of serum. A culture medium useful for the invention may be free of feeder cells or may be free of serum, or, in particular embodiments the culture medium is free of both feeder cells and serum. The invention provides, in particular aspects, a defined differentiation medium that is free or essentially free of undefined ingredients, non-human animal serum, or feeder cells. A culture that is free of serum or feeder cells is a culture that contains no detectable serum or feeder cells. A culture that is essentially free of serum contains less than about 1%, 0.5%, 0.1%, 0.05%, 0.01%, 0.001% or any intermediate percentage of serum. A culture that is essentially free of feeder cells contains less than about 500, 250, 100, 50, 10, 5, 1 or any intermediate number of feeder cells per square centimeter of culturing surface.

In other embodiments, a culture medium may be free or essentially free of Matrigel™, which is a an undefined gelatinous protein mixture secreted by mouse tumor cells that is commercially available from BD Biosciences (New Jersey, USA). Matrigel™ is considered an undefined ingredient because it contains unknown components as well as components in unknown amounts. A culture that is free of Matrigel™ contains no detectable Matrigel™. A culture that is essentially free of Matrigel™ contains less than about 0.2, 0.1, 0.05, 0.01, 0.005, 0.0001 mg/cm$^2$ or any intermediate concentration of Matrigel™.

One may obtain culturing conditions that are free or essentially free of serum or feeder cells or Matrigel™ by simply ensuring that such ingredients are not added to the medium. Moreover, to avoid inadvertent addition of serum or feeder cells, one may ensure that the components added to the differentiation medium lack serum, feeder cells, or undefined components. Alternatively, one may ensure that the differentiation medium is free or essentially free of animal-based feeder cells by using an antibody specific for a feeder cell of interest. For example, to ensure that a differentiation medium is free or substantially free of mouse embryonic fibroblasts, which are mouse-based feeder cells, one may use an antibody against mouse CD29. In a defined culture medium, no feeder cells, serum, or undefined ingredients are added to the culture.

The present invention, in certain aspects, provides for differentiation of pluripotent stem cells under a hypoxic atmosphere having less than about 5.5% oxygen for a period of time sufficient to generate progenitor cells. In these embodiments, a hypoxic atmosphere can comprise between about 0.5% oxygen gas and about 5.3% oxygen gas. In some embodiments, the hypoxic atmosphere can comprise between about 1.5% oxygen gas to about 5.3% oxygen gas, and a hypoxic atmosphere can comprise about 5% oxygen gas. In particular embodiments, the hypoxic atmosphere comprises about 5% oxygen gas, about 5% carbon dioxide gas, and about 90% nitrogen gas. In various embodiments, more than one differentiation step is included, and/or more than one type of medium is used. In such embodiments, one or more of such steps may include hypoxic atmospheric conditions.

In some embodiments, the methods include a step wherein the progenitor cells are harvested. In particular embodiments, progenitor cells are harvested after 4 days to 16 days of culturing. For example, hematopoietic progenitor cells may be harvested after 8 days to 12 days of culturing, or after 6 days to 9 days of culturing. Endothelial progenitor cells may be harvested, for example, after 6 days to 14 days of culturing.

In methods of the invention, the differentiation medium may include from about 5 ng/mL to about 200 ng/mL of BMP-4, VEGF, or bFGF. In other embodiments, the differentiation medium may include from about 25 ng/mL to about 75 ng/mL of BMP-4, VEGF, or bFGF. In particular embodiments, the differentiation medium may include about 50 ng/mL of BMP-4, VEGF, or bFGF. In other particular embodiments, the culture medium contains about 50 ng/mL of BMP-4, VEGF, and bFGF.

A differentiation medium useful for the invention may also include one or more amino acids, antibiotics, vitamins, salts, minerals, or lipids. In some embodiments, the medium contains one or more of the following: BIT 9500, BMP4, VEGF, bFGF, L-glutamine, non-essential amino acids, monothioglycerol, penicillin, or streptomycin. It is also contemplated that the medium may contain all of these listed ingredients, and it is further contemplated that the medium may contain one or more of the listed ingredients while specifically excluding one or more of these listed ingredients.

In particular embodiments, the culture medium contains about 20% BIT 9500, about 50 ng/mL BMP4, about 50 ng/mL VEGF, about 50 ng/mL bFGF, about 2 mM L-glutamine, about 0.1 mM non-essential amino acids, about 450 µM monothioglycerol, penicillin, and streptomycin. The culture medium may include a TeSR medium, such as TeSR1, TeSR2, or mTeSR, or the culture may include one or more of the ingredients present in a TeSR medium.

The differentiation medium useful in the present invention may include a survival factor. The survival factor may be, for example, an inhibitor of a Rho-associated kinase (ROCK), such as HA100 or H1152, or an inhibitor of myosin II, such as blebbistatin.

Methods of the invention, in some aspects, include more than one differentiation step. In such aspects, more than one differentiation medium may be employed. For example, a first differentiation medium may be used to initiate the differentiation of pluripotent stem cells into progenitor cells, followed by a step in which a second differentiation medium is used to expand and maintain the progenitor cells or to further differentiate the progenitor cells.

Such a second differentiation medium may include one or more of the following: BIT 9500, BMP4, VEGF, bFGF, L-glutamine, non-essential amino acids, monothioglycerol, penicillin. streptomycin, L-glutamine plus beta-mercaptoethanol (β-ME), FMS-like tyrosine kinase 3 ligand (FLT-3 ligand), stem cell factor (SCF), thrombopoietin (TPO), interleukin 3 (IL-3), interleukin 6 (IL-6), or heparin. In some embodiments, the second differentiation medium includes BIT 9500, non-essential amino acids, L-glutamine plus β-ME, FLT-3 ligand, TPO, IL-3, IL-6, and heparin. However, it is also contemplated that the second differentiation medium may contain one or more of these ingredients while specifically excluding one or more of these ingredients. In some embodiments, the second differentiation medium contains one or more of the following: amino acids, antibiotics, vitamins, salts, minerals, lipids, a TeSR medium, or one or more ingredients of a TeSR medium. In some embodiments, the second differentiation medium may include about 20% BIT 9500, about 1% non-essential amino acids, about 1% L-glutamine plus β-ME, about 25 ng/mL FLT-3 ligand, about 25 ng/mL SCF, about 25 ng/ML TPO, about 10 ng/mL IL-3, about 10 ng/mL IL-6, and about 5U/mL heparin. Such a medium may be useful for maintaining or expanding or further differentiating hematopoietic progenitor cells. In particular embodiments, this second differentiation medium is useful for differentiating hematopoietic progenitor cells.

In embodiments that utilize multiple differentiation steps or media, it is contemplated that any one differentiation step or differentiation medium may be specifically excluded. In addition, in a differentiation medium useful for the invention, the medium may specifically exclude one or more of the ingredients disclosed herein as potential components of a differentiation medium of the present invention.

In some aspects, pluripotent stem cells may be cultured or maintained in an undifferentiated state prior to culturing in a differentiation medium. For example, the pluripotent stem cells may be cultured or maintained in a TeSR medium prior to culturing in a differentiation medium. In certain embodiments, the culture medium used to maintain stem cells in an undifferentiated state contains a TeSR medium and an inhibitor of ROCK. In other embodiments, the culture medium used to maintain stem cells in an undifferentiated state contains a TeSR medium and an inhibitor of myosin II. In certain aspects, the culturing medium used to maintain stem cells in an undifferentiated step contains a matrix component, such as collagen, fibronectin, or an RGD peptide.

The progenitor cells generated by methods disclosed herein may be purified using, for example, a magnetic activated cell sorter (MACS), flow cytometry, or fluorescence-activated cell sorting (FACS). In particular embodiments, the progenitor cells are identified or purified based on the expression of cell markers including CD34, CD43, CD31, CD105, or Factor VIII. For example, hematopoietic progenitor cells or endothelial progenitor cells may be purified based on their expression of the CD34 marker, and in some embodiments, endothelial progenitor cells may be purified based on their expression of the CD31 marker. In certain embodiments, hematopoietic progenitor cells are purified based on their expression of the CD34 and CD43 markers.

Some methods of the invention include the steps of dispersing a pluripotent stem cell colony or clonal cell grouping to form dispersed essentially individual cells and seeding the dispersed cells into a culture that may contain a survival factor. For example, the cells may be seeded at a density of from about 10,000 stem cells per square centimeter of culturing surface to about 70,000 stem cells per square centimeter of culturing surface. In certain embodiments, the cells may be seeded at a density of from about 10,000 stem cells per square centimeter of culturing surface to about 50,000 stem cells per square centimeter of culturing surface, or at a density of from about 20,000 stem cells per square centimeter of culturing surface to about 70,000 stem cells per square centimeter of culturing surface. In certain embodiments, the cells may be dispersed by mechanical or enzymatic means. For example, the cells may be dispersed by treatment with an effective amount of one or more enzymes, such as trypsin or trypLE, or a mixture of enzymes such as Accutase®.

In certain aspects, methods of the invention may include the steps of seeding the pluripotent stem cells in a culturing medium, which may contain a matrix component and/or a survival factor, to form a culture; introducing a differentiation medium into the culture, wherein the differentiation medium is free or essentially free of feeder cells and includes at least one recombinant growth factor selected from the group consisting of BMP-4, VEGF, and bFGF; and differentiating the cells under a hypoxic atmosphere having less than about 5.5% oxygen for a period of time sufficient to generate progenitor cells. In certain embodiments, one or more of these steps may be employed to produce CD34+ progenitor cells, CD31+ progenitor cells, CD43+ progenitor cells, or CD34+ CD43+ progenitor cells. The progenitor cells may then be harvested, and they may further be sorted. At this point, the progenitor cells may be maintained, expanded, or further differentiated. For example, the invention provides methods for further differentiating CD34+ progenitor cells into, for example, erythrocytes, macrophages, granulocytes, megakaryocytes, dendritic cells, mast cells, or endothelial cells. The invention also provides methods for further differentiating CD31+ progenitor cells into endothelial cells or mesenchymal cells.

In certain embodiments, the invention provides a method for differentiating human pluripotent stem cells into progenitor cells, wherein the method includes using a robot to automate at least a portion of the method. For example, a plurality of the human embryonic stem cells may be cultured using a bioreactor.

In some aspects, the invention provides a differentiation medium that may be free or essentially free of feeder cells, serum, or both. In some embodiments, a differentiation medium is free or essentially free of Matrigel™. In other embodiments, a differentiation medium is a defined differentiation medium that is free or essentially free of undefined ingredients (such as, for example, Matrigel™), serum, and feeder cells. In yet other aspects, a differentiation medium may be free or essentially free of non-human animal growth factors. A differentiation medium may, in certain embodiments, be free or essentially free of non-human animal proteins. In particular embodiments, the differentiation medium is free of feeder cells, serum, and Matrigel™.

A differentiation medium of the invention may contain one or more of BMP-4, VEGF, and bFGF. A differentiation medium of the invention may comprise BMP-4 in an amount of from about 5 ng/mL to about 200 ng/mL, or about 50 ng/mL. The differentiation medium may comprise VEGF in an amount of from about 5 ng/mL to about 200 ng/mL, or about 50 ng/mL. The differentiation medium may comprise bFGF in an amount of from about 5 ng/mL to about 200 ng/mL, or about 50 ng/mL. In certain embodiments, the differentiation medium includes one or more amino acids, antibiotics, vitamins, salts, minerals, or lipids. In other embodiments, the differentiation medium contains a matrix component, such as fibronectin, collagen, or an RGD peptide. The differentiation medium may also contain a survival factor, such as an inhibitor of ROCK or an inhibitor of myosin II.

In some embodiments, a differentiation medium of the invention includes BIT 9500, BMP4, VEGF, bFGF, L-glutamine, non-essential amino acids, monothioglycerol, penicillin, or streptomycin. It is specifically contemplated that the differentiation medium may contain all of these ingredients, or it may contain one or more of these ingredients while specifically excluding one or more of these ingredients. In select embodiments, the differentiation medium may comprise about 20% BIT 9500, about 50 ng/mL BMP4, about 50 ng/mL VEGF, about 50 ng/mL bFGF, about 2 mM L-glutamine, about 0.1 mM non-essential amino acids, about 450 μM monothioglycerol, about 100 I.U. penicillin, and about 0.1 mg streptomycin. The differentiation medium may also contain one or more of the salts, minerals, lipids, amino acids, vitamins, or other components of a TeSR1, TeSR2, or mTeSR1 medium.

In certain aspects, a differentiation medium of the invention includes one or more of the following: beta-mercaptoethanol (β-ME), FMS-like tyrosine kinase 3 ligand (FLT-3 ligand), stem cell factor (SCF), thrombopoietin (TPO), interleukin 3 (IL-3), interleukin 6 (IL-6), or heparin. In some aspects, the differentiation medium contains one or more of BIT 9500, non-essential amino acids, L-glutamine plus β-ME, FLT-3 ligand, SCF, TPO, IL-3, IL-6, and heparin. In other embodiments, the differentiation medium may include BIT 9500, non-essential amino acids, L-glutamine plus β-ME, FLT-3 ligand, SCE, TPO, IL-3, IL-6, and heparin. However, it is specifically contemplated that the differentiation medium may include one or more of these ingredients while specifically excluding one or more of these ingredients. In certain embodiments, the differentiation medium contains about 20% BIT 9500, about 1% non-essential amino acids, about 1% L-glutamine plus β-ME, about 25 ng/mL FLT-3, ligand about 25 ng/mL SCF, about 25 ng/mL TPO, about 10 ng/mL IL-3, about 10 ng/mL IL-6, and about 5U/mL heparin.

In some embodiments, the invention regards a method for differentiating a human pluripotent stem cell into a CD31+ progenitor cell, CD34+ progenitor cell, or CD43+ progenitor cell. A culture medium used in such a method may contain a matrix component and at least one recombinant growth factor selected from the group consisting of BMP-4, VEGF, and bFGF. The culture may be free or essentially free of free of non-human animal serum, feeder cells, and Matrigel™. In certain embodiments, the culture may be free of non-human animal serum, feeder cells, and Matrigel™. In particular embodiments, the culture may be free or essentially free of non-human animal proteins. In some such methods, the pluripotent stem cell is cultured in a defined differentiation medium.

A differentiation medium of the invention may, in certain embodiments, be maintained under a hypoxic atmosphere having from about 0.5% oxygen gas to about 5.3% oxygen gas. The differentiation medium may also include a cell, such as a pluripotent stem cell, a progenitor cell, a hematopoietic progenitor cell, an endothelial progenitor cell, a CD34+ progenitor cell, a CD31+ progenitor cell, or a CD43+ progenitor cell.

The invention is, in some aspects, directed to kits comprising a differentiation culture medium in one or more sealed vials. For example, the kit may include a differentiation medium that is maintained under a hypoxic atmosphere having from about 0.5% oxygen gas to about 5.3% oxygen gas. The kit may also include a cell, such as pluripotent stem cell, a progenitor cell, a hematopoietic progenitor cell, or an endothelial progenitor cell.

The invention further contemplates methods of screening a candidate substance for an ability to affect differentiation of a pluripotent cell into a CD34+ progenitor cell, CD31+ progenitor cell, or CD43+ progenitor cell. For example, a pluripotent stem cell may be cultured in a culture medium that is free or essentially free of feeder cells and that includes: a matrix component, at least one recombinant growth factor (such as BMP-4, VEGF, and bFGF), and a candidate substance. The pluripotent stem cells may then be differentiated under a hypoxic atmosphere having less than 5.5% oxygen for a period of time to provide the progenitor cells. Then, the differentiation of the pluripotent stem cell into the desired progenitor cell may be assessed. In some embodiments, such a method screens for a candidate substance that promotes differentiation. In certain aspects, the step of assessing comprises comparing differentiation of the pluripotent stem cell in the presence of the candidate substance to differentiation of the pluripotent stem cell in a similar cell culture without the candidate substance. For example, assessing may include assessing one or more differentiation markers or assessing cellular morphology. In some embodiments, the candidate substance may include a small molecule, a peptide, a polypeptide, a protein, an antibody, an antibody fragment, or a nucleic acid.

In further aspects, the invention provides methods for treating a disease, disorder, or injury by administering to a subject a pharmaceutically effective amount of progenitor cells, hematopoietic cells, or endothelial cells obtained by methods disclosed herein. In certain aspects, the treatment provided may include erythrocytes, macrophages, granulocytes, megakaryocytes, dendritic cells, mast cells, or endothelial cells. For example, the disease may be a cardiovascular disease, and the treatment may include endothelial cells.

In further embodiments, the invention provides a clonal cell population, meaning that the population of cells is from a common ancestor (such as a pluripotent stem cell), that comprises progenitor cells (such as CD34+ progenitor cells, CD31+ progenitor cells, or CD43+ progenitor cells), wherein the population is in a defined medium. In some embodiments, the cell population is in a medium that is free or essentially free of feeder cells, serum, or both. The population may comprise 5%, 10%, 15%, 20%, 25%, 30%, 35%, 40%, 45%, 50%, 55%, 60%, 65%, 70%, 75%, 80%, 85%, 90%, 100% or any intermediate percentage of CD34+ or CD43+ progenitor cells. The population may comprise 20%, 25%, 30%, 35%, 40%, 45%, 50%, 55%, 60%, 65%, 70%, 75%, 80%, 85%, 90%, 100% or any intermediate percentage of CD31+ or CD34+ progenitor cells. In particular embodiments, the population comprises about $10^6$, $10^7$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or more progenitor cells, such as CD34+ progenitor cells, CD31+ progenitor cells, or CD43+ progenitor cells. In yet other embodiments, the invention provides populations of progenitor cells, such as CD34+ progenitor cells, CD31+ progenitor cells, or CD43+ progenitor cells, that are produced by the methods disclosed herein.

In methods of the invention, it is contemplated that any one step may be excluded or any one of the disclosed components of a composition may be excluded. In a differentiation medium of the invention, it is contemplated that any one of the disclosed ingredients may be excluded.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The present invention provides methods and compositions for the production of hematopoietic cells or endothelial cells from human pluripotent stem cells without the need for stromal cells or embryoid bodies. Some methods use a defined differentiation medium and may include hypoxic atmospheric conditions. These methods may be used to produce human hematopoietic progenitor cells, which may be further differentiated into cell lineages including erythrocyte, macrophages, granulocytes and/or megakaryocytes. In addition, the methods may be used to produce human endothelial progenitor cells, which may be further differentiated into endothelial cells. The differentiation medium of the present invention may contain growth factors (e.g., BMP-4, VEGF, bFGF) and may be used in conjunction with a matrix component, such as fibronectin.

I. Differentiation Medium

Traditional pluripotent stem cell culture methods have relied on serum products and mouse feeder layers for differentiating pluripotent stem cells into a variety of cell types. These procedures have limited the scale on which differentiation can be conducted, increased biological variability and potential contamination, and severely hampered the use of pluripotent stem cells in translational therapies in which they might otherwise prove useful.

Accordingly, the present invention provides a differentiation medium. The differentiation medium may be free or essentially free of feeder cells, free or essentially free of serum, or free or essentially free of feeder cells and serum. In certain embodiments, the differentiation medium is a defined medium that is free or essentially free of non-human animal serum or feeder cells.

In certain embodiments, the differentiation medium contains growth factors (e.g., BMP-4, VEGF, and bFGF). The differentiation medium may be used in conjunction with a matrix component such as fibronectin or collagen. The differentiation medium may also contain additional nutrients, amino acids, antibiotics, buffering agents, and the like.

The differentiation medium may contain Iscove's Modified Dulbecco's Medium (also called IMDM) (Invitrogen, Carlsbad, Calif.). In certain embodiments, the differentiation medium contains IMDM and one or more of the ingredients listed below in Table 1. It is also specifically contemplated that the differentiation medium contains one or more of the ingredients listed in Table 1, while specifically excluding one or more of the ingredients listed in Table 1. In other embodiments, the differentiation medium contains all of the ingredients listed in Table 1. In a preferred embodiment, the differentiation medium comprises the components listed in Table 1 in about the preferred concentrations indicated.

TABLE 1

IMDM-Based Differentiation medium

| Possible Ingredients | Preferred Concentration |
|---|---|
| BIT 9500 | 20% |
| BMP4 | 50 ng/mL |

TABLE 1-continued

IMDM-Based Differentiation medium

| Possible Ingredients | Preferred Concentration |
|---|---|
| VEGF | 50 ng/mL |
| bFGF | 50 ng/mL |
| L-glutamine | 2 mM |
| Non-essential amino acids | 0.1 mM |
| Monothioglycerol | 450 μM |
| Penicillin | 100 I.U. |
| Streptomycin | 0.1 mg/mL |

In some embodiments, the pluripotent stem cells are differentiated in one medium, such as a differentiation medium containing one or more of the components listed in Table 1, and then cultured in a second differentiation medium in order to maintain, expand, or further differentiate the progenitor cells. Such a second differentiation medium may contain one or more of the ingredients listed in Table 1, in addition to one or more of the following: beta-mercaptoethanol ((β-ME), FMS-like tyrosine kinase 3 ligand (FLT-3 ligand), stem cell factor (SCF), thrombopoietin (TPO), interleukin 3 (IL-3), interleukin 6 (IL-6), or heparin. In some aspects, the second differentiation medium contains one or more of the ingredients listed in Table 1 plus IMDM, β-ME, FLT-3 ligand, SCF, TPO, IL-3, IL-6, and heparin. In some embodiments the second differentiation medium contains IMDM, BIT 9500, non-essential amino acids, L-glutamine plus β-ME, FLT-3 ligand, SCF, TPO, IL-3, IL-6, and heparin; however, it is also specifically contemplated that the second differentiation medium contains one or more of these ingredients while specifically excluding one or more of these ingredients. In a preferred embodiment, the second medium comprises IMDM and further comprises: about 20% BIT 9500, about 1% non-essential amino acids, about 1% L-glutamine plus β-ME, about 25 ng/mL FLT-3 ligand, about 25 ng/mL SCF, about 25 ng/mL TPO, about 10 ng/mL IL-3, about 10 ng/mL IL-6, and about 5U/mL heparin. In a particular embodiment, the second differentiation medium is used to maintain and expand hematopoietic progenitor cells.

After cells are cultured in a differentiation medium of the present invention, the cells may be harvested. For example, the cells may be harvested after 1, 2, 3, 4, 5, 6, 7, 8, 9, 10, 11, 12, 13, 14, 15, 16, 17, 18, 19, or 20 days of culturing. In some embodiments, the cells are harvested after 4 to 14 days of culturing. In preferred embodiments, the pluripotent stem cells may be differentiated for 8 days to 12 days, from 6 days to 9 days, or from 6 days to 10 of culturing.

A. Growth Factors

Various growth factors are known in the art and may be used with the present invention. In certain embodiments, a differentiation medium of the present invention may contain one, two, or more growth factors such as, for example, BMP-4, VEGF, and bFGF. These growth factors can be used to differentiate human embryonic stem cells into hematopoietic and endothelial cells using a mouse embryonic fibroblast culture system (Wang et al., 2007).

Growth factors which may be comprised in a differentiation medium of the present invention include, but are not limited to, BMP-4, VEGF, bFGF, stem cell factor (SCF), flt-3 ligand, interleukin 3 (IL-3), interleukin 6 (IL-6), interleukin 9 (IL-9), interleukin 11 (IL-11), insulin related growth factor 1 (IFG1), insulin related growth factor 2 (IGFII), erythropoietin (EPO), thrombopoietin (TPO), granulocyte-macrophage-colony-stimulating factor (GM-CSF), and granulocyte colony-stimulating factor (G-CSF). A differentiation medium of the present invention may contain one, two, three, or more of these factors; for example, other growth factors may be included in a defined medium in order to increase proliferation or modulate the differentiation state of the cells. Various amounts of these factors may be used to stimulate cellular responses (e.g., in the amounts described in Yamamura et al., 2007; Fadilah et al., 2007; Bashey et al., 2007).

1. BMP-4

Bone morphogenetic protein-4 (BMP-4) is a member of the group of bone morphogenic proteins and a ventral mesoderm inducer. BMPs are expressed in adult human bone marrow (BM) and are important for bone remodeling and growth. In certain embodiments, inclusion of BMP4 is only needed for the first two to three days in culture, after which time it can be removed from the system with no detrimental effect on differentiation.

BMP-4 is important for the modulation of the proliferative and differentiative potential of hematopoietic progenitor cells (Bhardwaj et al., 2001; Bhatia et al., 1999; Chadwick 2003). Additionally, BMP-4 can modulate early hematopoietic cell development in human fetal, neonatal, and adult hematopoietic progenitor cells (Davidson and Zon, 2000; Huber et al., 1998; Marshall et al., 2000). For example, BMP-4 can regulate the proliferation and differentiation of highly purified primitive human hematopoietic cells from adult and neonatal sources (Bhatia et al., 1999), and BMP-4 can promote hematopoietic differentiation in human embryonic stem cells (Chadwick, 2003). BMP-4 can also promote differentiation of endothelial cells from endothelial progenitor cells (Wang et al., 2007).

In certain embodiments, BMP-4 is included in a differentiation medium of the present invention at a concentration of from about 2.5 to about 500 ng/mL, from about 5 to about 500 ng/mL, from about 5 to about 200 ng/mL, from about 5 to about 100 ng/mL, from about 25 to about 200 ng/mL, from about 25 to about 75 ng/mL, or any range derivable therein. In certain embodiments, BMP-4 is included in the differentiation medium at a concentration of about 2.5, 5, 10, 15, 20, 25, 30, 35, 40, 45, 50, 55, 60, 65, 70, 75, 80, 85, 90, 95, or about 100 ng/mL.

2. VEGF

Vascular endothelial growth factor (VEGF) is an important signaling protein that is involved in formation of the embryonic circulatory system and angiogenesis. VEGF can affect a variety of cell types including vascular endothelium and other cell types (e.g., neurons, cancer cells, kidney epithelial cells). In vitro, VEGF can stimulate endothelial cell mitogenesis and cell migration. VEGF function has also been shown to be important in a variety of disease states including cancer, diabetes, autoimmune diseases, and ocular vascular diseases.

In certain embodiments, VEGF is included in a differentiation medium of the present invention at a concentration of from about 2.5 to about 500 ng/mL, from about 5 to about 500 ng/mL, from about 10 to about 200 ng/mL, from about 5 to about 100 ng/mL, from about 25 to about 200 ng/mL, from about 25 to about 75 ng/mL, or any range derivable therein. In certain embodiments, VEGF is included in the differentiation medium at a concentration of about 2.5, 5, 10, 15, 20, 25, 30, 35, 40, 45, 50, 55, 60, 65, 70, 75, 80, 85, 90, 95 or about 100 ng/mL.

3. bFGF

Basic fibroblast growth factor (bFGF, also referred to as FGF-2), is a growth factor that has been implicated in diverse biological processes, including limb and nervous system development, wound healing, and tumor growth. Previous studies have indicated that bFGF is unlikely to affect hematopoietic cell development or survival (Ratajczak et al., 1996.), although bFGF has been used to support feeder-independent growth of human embryonic stem cells (Ludwig et al., 2006a). In certain embodiments, bFGF is not required to induce differentiation; thus, in various embodiments it may be included or excluded in a medium of the present invention.

In certain embodiments, bFGF is included in a differentiation medium of the present invention at a concentration of from about 2.5 to about 500 ng/mL, from about 5 to about 500 ng/mL, from about 10 to about 200 ng/mL, from about 5 to about 100 ng/mL, from about 25 to about 200 ng/mL, from about 25 to about 75 ng/mL, or any range derivable therein. In certain embodiments, bFGF is included in the differentiation medium at a concentration of about 2.5, 5, 10, 15, 20, 25, 30, 35, 40, 45, 50, 55, 60, 65, 70, 75, 80, 85, 90, 95 or about 100 ng/mL. It is envisioned that, in certain embodiments, other fibroblast growth factors such as acidic FGF (aFGF), FGF4, FGF9, FGF17 or FGF18 may substituted for or included with bFGF, e.g., at the concentrations described above.

4. SCF

SCF (also known as SCF, kit-ligand, KL, or steel factor) is a cytokine that plays a role in hematopoiesis, spermatogenesis, and melanogenesis. In methods of the invention, SCF may be included in a medium in a concentration of about 2.5, 5, 10, 15, 20, 25, 30, 35, 40, 45, 50, 55, 60, 65, 70, 75, 80, 85, 90, 95 or about 100 ng/mL. In a preferred embodiment SCF is included in a medium at a concentration of about 25 ng/mL.

5. TPO

TPO also plays a role in differentiation of hematopoietic progenitor cells into, for example, megakaryocytes. In methods of the invention, TPO may be included in a medium in a concentration of about 2.5, 5, 10, 15, 20, 25, 30, 35, 40, 45, 50, 55, 60, 65, 70, 75, 80, 85, 90, 95 or about 100 ng/mL. In a preferred embodiment TPO is included in a medium at a concentration of about 25 ng/mL.

B. Survival Factors

In select embodiments, a differentiation medium of the present invention may be used to seed, culture, maintain, or differentiate pluripotent stem cells and may contain a survival factor. Survival factors may be used to enhance the survival and differentiation efficiency of individualized pluripotent stem cells using methods of the present invention. Survival factors that may be used in some embodiments include, but are not limited to, inhibitors of myosin II, inhibitors of the Rho-independent kinase (ROCK), and inhibitors of protein kinase C (PKC). In certain embodiments, a survival factor may be included in a culturing medium comprising TeSR1, TeSR2, or mTeSR medium.

Exemplary survival factors or their cell culture compatible salts that may be useful with a method described herein may include, but are not limited to: a myosin II inhibitor, such as blebbistatin or a pyridazinyl compound (US 20080021035); a ROCK inhibitor such as HA100, H1152, (+)-trans-4-(1-aminoethyl)-1-(pyridin-4-ylaminocarbonyl)cyclohexane dihydro-chloride monohydrate (WO 00078351, WO 00057913), imidazopyridine derivatives (U.S. Pat. No. 7,348,339), substituted pyrimidine and pyridine derivatives (U.S. Pat. No. 6,943,172) or substituted isoquinoline-sulfonyl compounds (EP 00187371); or a PKC inhibitor such as a V5 peptide (U.S. Pat. No. 7,459,424), polymyxin B, calphostin C, palmitoyl-DL-carnitine, stearoylcarnitine, hexadecylphosphocholine, staurosporine and its derivatives, sangivamycin; safingol, D-erythro-sphingosine; chelerythrine chloride, melittin; dequalinium chloride; ellagic acid, HBDDE, 1-O-hexadecyl-2-O-methyl-rac-glycerol, Hypercin, K-252, NGIC-J, Phloretin, piceatannol, tamoxifen citrate, or substituted piperazines or thiazines (U.S. Pat. No. 6,815,450).

C. Other Components

A differentiation medium of the present invention may also contain additional components such as nutrients, amino acids, antibiotics, buffering agents, and the like. In certain embodiments a differentiation medium of the present invention may contain non-essential amino acids, L-glutamine, penicillin, streptomycin, and monothioglycerol.

BIT 9500 (StemCell Technologies Inc., Vancouver, Canada) may also be included in a differentiation medium of the present invention, e.g., in an amount of about from about 10% to about 30%, or in an amount of about 20%. BIT 9500 contains pre-tested batches of bovine serum albumin, insulin and transferrin (BIT) in Iscove's MDM. BIT 9500 contains 50 mg/mL bovine serum albumin (buffered with $NaHCO_3$), 50 µg/mL insulin, 1 mg/mL human transferrin (iron-saturated). In certain embodiments, Serum Replacement 3 (Sigma, catalog no. S2640) may be used in place of BIT 9500. In other embodiments, KOSR may be substituted for BIT 9500 in embodiments where a defined medium is not required. KOSR is an undefined medium that is commercially available (e.g., from Gibco/Invitrogen, catalog #10828) and has been described previously in WO 98/30679.

The use of BIT, as described above, may be replaced by HIT; HIT includes the compositions described above for BIT, with the exception that the components, such as serum albumin, are human components (e.g., human serum albumin). For example, the use of HIT may be preferable in embodiments where the risk of a possible infection etc. is of particular concern.

Heparin may also be included in a medium of the invention. For example, heparin may be useful in a differentiation medium to promote further differentiation of hematopoietic progenitor cells. Heparin may be included at a concentration of about 1, 2, 3, 4, 5, 6, 7, 8, 9, or 10 U/mL. In a preferred embodiment heparin is included in the medium at a concentration of 5 U/mL.

In various embodiments, a differentiation medium may contain one or more vitamins, minerals, salts, lipids, amino acids, or other components. For example, a defined medium of the present invention may contain one or more components present in a TeSR medium, e.g., at the same or a comparable concentration as is included in the TeSR media described below.

II. Matrix Component

A differentiation medium of the present invention is preferably employed in a method described herein with one or more matrix components, such as fibronectin, collagen, or an RGD peptide. Without wishing to be bound by any theory, matrix components may provide a solid support for the growth of pluripotent stem cells. In preferred embodiments, a matrix component is applied to a culturing surface and contacted with the culture medium and cells.

Various matrix components may be used with the present invention including a collagen such as collagen IV, laminin, vitronectin, Matrigel™, gelatin, polylysine, thrombospondin (e.g., TSP-1, -2, -3, -4 and/or -5), and/or ProNectin-F™. In certain embodiments, the use of only Matrigel™, collagen IV, or laminin with cells previously cultured using TeSR may be avoided due to possible adverse effects on cell viability; nonetheless, these compositions may be advantageously used in combination with other matrix components. Combinations of these matrix components may provide additional benefits for promoting cell growth and cell viability. In certain embodiments, 1, 2, 3, 4, 5, 6, or more of the above matrix components may be used to culture cells and/or differentiate embryonic stem cells into hematopoietic progenitor cells.

1. Fibronectin

Fibronectin may be used as a matrix component in a defined cell culture medium of the present invention. Without wishing to be bound by any theory, fibronectin may provide a substrate for human embryonic stem cells to grow and differentiate without the use of feeder cells or embryoid bodies.

Fibronectin is a high-molecular-weight glycoprotein containing about 5% carbohydrate. Fibronectin can bind integrins and extracellular matrix components such as collagen, fibrin and heparan sulfate. Fibronectin has been implicated in functions including wound healing and the development of cancer, and fibronectin is also important for proper neural crest formation in mammalian cells.

In certain embodiments, fibronectin is included in a differentiation medium of the present invention at a concentration of from about 1 $\mu g/cm^2$ to about 10 $\mu g/cm^2$, or from about 3 $\mu g/cm^2$ to about 5 $\mu g/cm^2$. Fibronectin may be included in a differentiation medium at a concentration of about 2.5, 3, 3.5, 4, 4.5, or about 5 $\mu g/cm^2$.

2. Collagen

Collagen may be used as a matrix component in a cell culture medium of the present invention. Collagen is the major protein component of connective tissue, and is a major component of the extracellular matrix that supports tissues and cells. As with fibronectin, although not wishing to be bound by any theory, collagen may provide a substrate for human embryonic stem cells to grow and differentiate without the use of feeder cells or embryoid bodies. Collagen may be included in a differentiation medium of the present invention at a concentration of about, for example, about 0.5 $\mu g/cm^2$-5 $\mu g/cm^2$ or about 1.5 $\mu g/cm^2$. In certain embodiments, collagen may be used to coat a surface for culturing cells. In certain aspects, the collagen useful in the methods disclosed is collagen IV.

3. RGD Peptides

RGD peptides may be used as a matrix component in a defined cell culture medium of the present invention. RGD peptides are adhesive proteins that contain the Arg-Gly-Asp (RGD) sequence, and certain RGD peptides may play an important role in cell adhesion, migration, and growth. Without wishing to be bound by any theory, RGD peptides may provide a physical substrate for embryonic stem cells, similar to fibronectin, to allow for the differentiation and growth of embryonic stem cells. In certain embodiments, synthetic RGD peptides may be utilized with the present invention.

RGD peptides may be included in a differentiation medium of the present invention at a concentration of about, for example, about 0.05-0.2 mg/mL or about 0.1 mg/mL. In certain embodiments, ProNectin F may be used to coat a surface for culturing of cells. PRONECTIN F (PnF) is a commercially available RGD peptide that typically contains 13 sites of an arginine-glycine-aspartic acid (RGD).

III. Hypoxia and Differentiation

In accordance with the convention of the art (Ezashi et al., 2005), ambient oxygen concentration is referred to herein as normoxic. As used herein, a "hypoxic atmosphere" refers to an atmosphere comprising less oxygen than ambient air, which includes approximately 15-25% oxygen. Preferably, a hypoxic atmosphere contains less than about 5.5% oxygen.

In certain embodiments of the present invention, a method is provided for differentiating pluripotent stem cells that involves culturing the cells in a hypoxic atmosphere. The hypoxic atmosphere may comprise a mixture of gases that are compatible with known methods in the art and may specifically comprise an amount of oxygen gas that is less than about 5.5% volume of the total atmospheric gas volume. In some embodiments, the hypoxic atmosphere comprises between about 1% oxygen gas and about 5.5% oxygen gas. In other embodiments, the hypoxic atmosphere comprises 5% oxygen gas. In preferred embodiments, the hypoxic atmosphere comprises 5% $CO_2$, 5% $O_2$, and 90% $N_2$. The atmospheric conditions useful for a method of the present invention may be accomplished by any means known in the arts of cell culture and compressed gas delivery.

IV. Preparation and Maintenance of Pluripotent Stem Cells

The term "pluripotency" is generally used in the art of cell biology to refer to the capacity of a cell to differentiate into any of the cell types arising from the three germ layers, ectoderm, endoderm, and mesoderm, that develop during embryogenesis. The terms "pluripotent cells" and "pluripotent stem cells" are used herein to describe cells that have the capacity to differentiate into essentially any human fetal or adult cell type. Exemplary types of pluripotent stem cells may include, but are not limited to, embryonic stem cells and induced pluripotent stem cells (or iPS cells). As used herein, the term "embryonic stem cell" or "pluripotent stem cell" may refer to cells that naturally occur in or are derived from a blastocyst, as well as to cells that have been induced to become pluripotent or to return to a stem-cell-like state (see, e.g., Nakagawa et al., 2007; Yu et al., 2007).

A "progenitor cell," as used herein, refers to a lineage-committed cell derived from a pluripotent stem cell. Thus, progenitor cells are more differentiated than pluripotent stem cells. In some embodiments, a progenitor cell is a hematopoietic progenitor cell, an endothelial progenitor cell, or a hematoendothelial progenitor cell.

Pluripotent stem cells that may be used with the present invention may be cultured and maintained in an undifferentiated state using a variety of methods, as would be known to one of ordinary skill in the art. For example, methods for culturing human pluripotent stem cells may utilize either fibroblast feeder cells or a medium that has been exposed to fibroblast feeder cells in order to maintain the stem cells in an undifferentiated state. In preferred embodiments, human pluripotent stem cells that are differentiated according to methods of the present invention are first cultured in an undifferentiated state using a feeder-independent culture system, such as the TeSR1 medium, TeSR2 medium, or mTeSR medium described herein.

It is anticipated that virtually any human pluripotent stem cell line may be used with the present invention, e.g., differentiated into hematopoietic progenitor cells or endothelial progenitor cells using a defined cell culture medium. For example, human embryonic stem cell line H1, H9, hES2, hES3, hES4, hES5, hES6, BG01, BG02, BG03, HSF1, HSF6, H1, H7, H9, H13B, and/or H14 etc. may be used with the present invention. It is further anticipated that stem cell lines that subsequently become available may also be used with the present invention. Although human pluripotent stem cells are preferably used with the present invention, in some instances, other pluripotent stem cells, such as mammal, mouse, primate, etc., may be used in methods of the present invention.

In certain embodiments, induced pluripotent stem cells (iPS cells) may be cultured and/or differentiated into hematopoietic cells or endothelial cells according to the present invention. Induced pluripotent stem cells are reprogrammed somatic cells that exhibit stem cell pluripotency and express embryonic markers (Takahashi et al., 2007; Takahashi et al., 2007; Nakagawa et al., 2007). Methods of producing iPS cells are known in the art, and essentially any appropriate method of reprogramming a somatic cell may be used to produce a pluripotent stem cell for use in a method disclosed herein. Exemplary methods of generating iPS cells may include, for example, methods disclosed by Thomson (US 2008/

0233610) and by Daley and coworkers (US 2009/0004163), both incorporated herein by reference in their entirety.

A. TeSR Medium

TeSR medium is a defined medium which may be used to culture undifferentiated human pluripotent stem cells. TeSR includes bFGF, LiCl, γ-aminobutyric acid (GABA), pipecolic acid and TGFβ, and various methods utilizing TeSR have been described previously, e.g., in U.S. Application 2006/0084168 and Ludwig et al. (2006a; 2006b), which are incorporated herein by reference in their entirety. The term "TeSR medium," as used herein, encompasses TeSR1 medium, TeSR2 medium, or mTeSR medium. TeSR2 medium (Stem Cell Technologies, Vancouver, BC, Canada) is essentially identical to TeSR1 medium, and, like TeSR1, TeSR2 medium is humanized. TeSR1 medium, TeSR2 medium, or mTeSR medium may be used in the methods disclosed herein.

TeSR medium typically includes inorganic salts, trace minerals, energy substrates, lipids, amino acids, vitamins, growth factors, proteins, and other components. The complete formulation for TeSR1 medium is described in at least U.S. Pat. No. 7,442,548, which is incorporated herein by reference in its entirety.

Certain components in the TeSR formulation may also be substituted, e.g., in order to facilitate the use of the medium for research or to minimize costs. For example, the medium mTeSR1 may be used with the present invention and may differ from TeSR1 in the following ways: bovine serum albumin (BSA) is substituted for human serum albumin, and cloned zebrafish basic fibroblast growth factor (zbFGF) is substituted for human bFGF. TeSR1 is further described, e.g., in Ludwig et al. (2006), which is incorporated by reference herein in its entirety without disclaimer.

B. Matrix Component

Various matrix components may be used in culturing and maintaining human pluripotent stem cells. For example, one or more of collagen, fibronectin, laminin, or vitronectin may be used to coat a culturing surface as a means of providing a solid support for pluripotent cell growth, as described in Ludwig et al. (2006), which is incorporated by reference in its entirety. In one embodiment, the collagen is collagen IV.

Matrigel™ may also be used to provide a substrate for cell culture and maintenance of human pluripotent stem cells. Matrigel™ is a an undefined gelatinous protein mixture secreted by mouse tumor cells that is commercially available from BD Biosciences (New Jersey, USA). This mixture resembles the complex extracellular environment found in many tissues and is used by cell biologists as a substrate for cell culture. Methods for human pluripotent stem cell culture and maintenance are described, e.g., in Ludwig et al. (2006), which is incorporated by reference herein in its entirety. It is appreciated that additional methods for the culture and maintenance of human pluripotent stem cells, as would be known to one of ordinary skill in the art, may be used with the present invention.

V. Seeding and Differentiation of Pluripotent Stem Cells

Pluripotent stem cells that may be used with the present invention may be seeded into seeding medium using any method known in the art of cell culture. For example, pluripotent stem cells may be seeded as a single colony or clonal group into seeding medium, or pluripotent stem cells may be seeded as essentially individual cells. In some embodiments, pluripotent stem cells are separated into essentially individual cells using mechanical or enzymatic methods known in the art. By way of non-limiting example, pluripotent stem cells may be exposed to a proteolytic enzyme that disrupts the connections between the cells and between the cells and the culturing surface. Enzymes that may be used to individualize pluripotent stem cells for differentiation may include, but are not limited to, trypsin, in its various commercial formulations, trypLE (a stable trypsin-like enzyme available from Invitrogen, Carlsbad, Calif.), or a mixture of enzymes such as Accutase®.

In select embodiments, pluripotent cells may be added or seeded as essentially individual (or dispersed) cells to a culturing medium. The culturing medium into which cells are seeded may comprise TeSR medium or mTeSR medium and a survival factor as described herein. Preferably, dispersed pluripotent cells are seeded into a culturing medium at a density of less than 75,000 stem cells per square centimeter of culturing surface. In some embodiments, pluripotent cells are seeded at a density of from about 10,000 stem cells per square centimeter of culturing surface to about 70,000 stem cells per square centimeter of culturing surface. In these embodiments, a culturing surface may be comprised of essentially any material that is compatible with standard aseptic cell culture methods in the art. A culturing surface may additionally comprise a matrix component as described herein. In preferred embodiments, a matrix component may be applied to a culturing surface before contacting the surface with cells and medium.

In an aspect, the present invention provides a method of differentiating pluripotent cells in which pluripotent cells are seeded in culturing medium with or without a survival factor, cultured in a differentiation medium comprising one or more growth factors, and maintained under a hypoxic atmosphere. For methods described herein, the culturing medium and the differentiation medium may each be free or essentially free of feeder cells, and the method may further comprise harvesting differentiated cells, that is, hematopoietic progenitor cells or endothelial progenitor cells, at 4 to 14 days of culturing after seeding. In preferred embodiments, the progenitor cells are differentiated for 8 days to 12 days, from 6 days to 9 days, or from 6 days to 10 of culturing after seeding.

VI. Separation of Hematopoietic Progenitor Cells and Endothelial Cells

After preparation of hematopoietic stem cells and endothelial progenitor cells from embryonic stem cells, it may be desirable to purify the hematopoietic progenitor cells or endothelial progenitor cells. Methods for separation of cells using flow cytometry, such as FACS, or MACS may be used to separate or substantially purify a subset of cells, such as hematopoietic progenitor cells or endothelial progenitor cells, from a heterogeneous cell population.

A. Magnetic Activated Cell Sorting (MACS)

To isolate hematopoietic cells, CD34+ or CD43+ cells may be isolated from differentiated human embryonic stem cells (hESCs) using a magnetic activated cell sorter (MACS). MACS typically utilizes an antibody, such as a anti-CD34 antibody, in combination with magnetic beads to separate cells over a column. MACS may, in certain embodiments, be more gentle on cells and favorably affect cell viability and integrity as compared to FACS.

To isolate endothelial cells, MACS may be used to isolate CD31+ cells from differentiated hESCs.

Various MACS products are commercially available, including MACS MicroBeads™ columns or AutoMACS™ (Miltenyi Biotec, CA, USA), which may be used according to the manufacturer's instructions. PBS/0.5% BSA with 2 mM EDTA may be used as the buffer for cell isolation. In some experiments, a Dead Cell Removal Kit (Miltenyi Biotec) may be used to remove dead cells prior to isolation of CD34+ cells. Repeated MACS columns may be used if necessary.

B. Fluorescence Activated Cell Sorting (FACS)

Fluorescence activated cell sorting (FACS) may also be used to separate hematopoietic CD34+ cells or endothelial CD31+ cells. As is well known in the art, FACS utilizes the degree or fluorescence exhibited by a cell, e.g., due to bound anti-CD34 antibodies comprising a fluorescent tag, to separate cells. In this way, FACS may be used to separate hematopoietic CD34+ cells or endothelial CD31+ cells from a heterogeneous cell population.

VII. Differentiation of Hematopoietic Progenitor Cells

Various approaches may be used with the present invention to further differentiate hematopoietic progenitor cells into cell lineages including erythrocyte, granulocyte, macrophage, megakaryocyte, dendritic cell, and mast cell. These approaches may include the use of erythroid differentiation medium, methylcellulose, and megakaryocyte differentiation medium. In certain embodiments, hematopoietic progenitor cells may also be differentiated into endothelial cells or used to produce blood vessels.

These cell lineages may be used in a variety of medical treatments and applications. For example, erythrocyte lineages may be used in the production of blood for blood transplants. In other embodiments, endothelial cells may be used to produce new blood vessels, which may be used to treat an injury, such as a regional ischemia. Alternately, in certain embodiments, hematopoietic cells differentiated according to the invention may be administered to treat a disease such as sickle cell anemia (Hanna et al., 2007).

In vitro assay systems have been developed to quantify multi-potential progenitors and lineage-restricted progenitors of the erythrocyte, granulocyte, monocyte-macrophage, and megakaryocyte myeloid cell lineages. The colony-forming cells (CFCs) may be classified and enumerated based on the morphological recognition of one or more types of hematopoietic lineage cells within the colony. Colony evaluation and enumeration can be done in situ by light microscopy or by plucking individual colonies and then staining the cells using cytochemical and immunocytochemical methods. Various gelling agents including agar, agarose, methylcellulose, collagen and fibrin clots have been used for CFC assays.

In some embodiments, the further differentiation occurs in a second differentiation medium. Such a second medium may contain one or more of the ingredients listed in Table 1, in addition to one or more of the following: beta-mercaptoethanol (β-ME), FMS-like tyrosine kinase 3 ligand (FLT-3 ligand), stem cell factor (SCF), thrombopoietin (TPO), interleukin 3 (IL-3), interleukin 6 (IL-6), or heparin. In a preferred embodiment, the second medium comprises IMDM and further comprises: about 20% BIT 9500, about 1% non-essential amino acids, about 1% L-glutamine plus β-ME, about 25 ng/mL FLT-3 ligand, about 25 ng/mL SCF, about 25 ng/mL TPO, about 10 ng/mL IL-3, about 10 ng/mL IL-6, and about 5U/mL heparin.

A. Erythroid Differentiation Medium

Hematopoietic progenitor cells may be differentiated into erythroid cells using, e.g., an erythroid differentiation medium. An erythroid differentiation medium may be a serum-free or defined medium, and the medium may contain SCF, EPO, insulin, dexamethasone, and/or transferrin (Slukvin et al., 2007).

B. Methylcellulose

Methylcellulose may be used to induce differentiation of erythrocytes, macrophages and/or granulocytes from hematopoietic progenitor cells. Methylcellulose is a relatively inert polymer that forms a stable gel with good optical clarity. It is commonly used at a final concentration of about 0.9-1.2% in culture medium supplemented with compounds including fetal bovine serum (FBS), bovine serum albumin (BSA), 2-mercaptoethanol, insulin, transferrin, recombinant cytokines, or conditioned medium, which is a source of colony-stimulating factors. Methods involving methylcellulose differentiation of cells are described, e.g., in Kaufman et al. (2001).

Methylcellulose-based medium permits better growth of erythroid lineage cells than other types of semi-solid matrices, thus allowing the assay of erythroid, granulocyte, monocyte and multi-potential CFCs within the same culture. Megakaryocyte progenitors are suitably cultured in supplemented collagen-based medium and specifically identified using immunocytochemical staining.

C. Megakaryocyte Differentiation Medium

A megakaryocyte differentiation medium may be used to induce generation of megakaryocytes. Various products and approaches for the generation of megakaryocytes have been described and may be used with the present invention, such as described in WO 2006/050330. Additionally, Megacult™ is available from Stem Cell Technologies (Vancouver, BC, Canada) and may be used for producing/differentiating megakaryocytes. In various embodiments, thrombopoietin (TPO), interleukin 3 (IL-3), interleukin 6 (IL-6), Flt-3 ligand, and/or stem cell factor may be included in a megakaryocyte differentiation medium. Methods for megakaryocyte differentiation of cells are described, e.g., in Kaufman et al. (2001).

D. Endothelial Cell Generation

The CD34+ population derived by a method described herein may also contain hematoendothelial (or hemangioblast) and endothelial progenitors. Endothelial cells may be generated, for example, using the following protocol and may be used for implantation into an animal or human subject. Human ES cell-derived CD34+ cells may be cultured in either EGM™-2 medium (Lonza, Walkersville, Md.) or differentiation medium with 50 ng/mL rhVEGF and 5 ng/mL rhFGF-2 for 7 to 10 days. Endothelial cells may be suspended in about 1 mL solution of collagen (1.5 mg/mL) such as rat-tail type 1 collagen (BD Biosciences, Bedford, Mass.) and human plasma fibronectin (90 mg/mL) (Sigma) in 25 mM Hepes (Sigma) buffered EGM™ medium at 4° C. The pH may be adjusted to 7.4 by using 1N NaOH (Fisher Science, NJ). The cell suspension can then be pipetted into 12-well plates (Falcon) and warmed to 37° C. for 30 minutes to allow polymerization of collagen. Each solidified gel construct may be covered by one mL of warmed EGM medium. The cells may be cultured for about one day in 5% $CO_2$. In certain embodiments, cells may be verified as truly endothelial by growing cells within a thick layer of Matrigel™ to look for the formation of tubular structures, which formation serves as a marker for the endothelial phenotype.

VIII. Differentiation of Endothelial Progenitor Cells

Methods of the invention may be used to differentiate endothelial cells from embryonic stem cells. In some embodiments, the methods include initial steps differentiating embryonic stem cells into endothelial progenitor cells, followed by additional steps to sort and further differentiate the endothelial progenitor cells into endothelial cells. For example, stem cells (such as hESCs or iPS cells) may be seeded and grown as described herein. In some embodiments, hESCs or iPS cells are seeded using a matrix component, such as fibronectin or collagen-coated plates. In certain embodiments, cells are seeded onto a solid substrate that is at least partially coated with a matrix component. The cells may be seeded from about 10,000 stem cells per square centimeter of culturing surface to about 80,000 stem cells per square centimeter of culturing surface. In particular embodiments, the cells are seeded at a density from about 20,000 stem cells per square centimeter of culturing surface to about 70,000 stem cells per square centimeter of culturing surface. The cells may be cultured in TeSR medium that may contain a myosin II inhibitor, such as blebbistatin, or a ROCK inhibitor, such as H1152.

In some embodiments, the cells are grown overnight under low oxygen conditions, such as a hypoxic atmosphere having less than about 5.5% oxygen. The cells may then be grown in a medium containing one or more of the ingredients listed in Table 1. In certain embodiments, the medium contains all ingredients listed in Table 1.

After the cells have sufficiently grown and differentiated, the endothelial progenitor cells may be separated from other cells. For example, the cells may be magnetically sorted (using MACS technology) based on the expression of the cell surface marker CD31. The sorted endothelial progenitor cells may be further differentiated and expanded using a matrix component and a medium comprising one or more of the ingredients listed in Table 1. In some embodiments, this second differentiation medium comprises all of the ingredients listed in Table 1, and, in certain embodiments, the second differentiation medium contains all of the ingredients listed in Table 1 in the preferred concentrations listed. In a particular embodiment, the second differentiation medium comprises all of the ingredients listed in Table 1, and the bFGF concentration is about 1 ng/mL to about 50 ng/mL or about 5 ng/ml. The cells may then be expanded and assayed for functionality.

IX. Bioreactors and Automation

One or more steps for the culture of stem cells and/or differentiation of hematopoietic progenitor cells and endothelial progenitor cells from pluripotent stem cells may be automated. Automating a process using robotic or other automation can allow for more efficient and economical methods for the production, culture, and differentiation of cells. For example, robotic automation may be utilized as described in US patent application 20090029462, incorporated herein by reference in its entirety.

A bioreactor may also be used in conjunction with the present invention to culture, maintain, and/or differentiate cells (e.g., human embryonic stem cells, CD34+ cells, CD31+ cells, hematopoietic cells, etc.) according to the present invention. Bioreactors provide the advantage of allowing for the "scaling up" of a process in order to produce an increased amount of cells. Various bioreactors may be used with the present invention, including batch bioreactors, fed batch bioreactors, continuous bioreactors (e.g., a continuous stirred-tank reactor model), and/or a chemostat.

In certain embodiments, the Tecan Cellerity system may be used with the present invention. hESCs may be cultured on the robot, using flat plates in order to induce differentiation into CD34/43+ cells. Once separation of the cells has occurred, spinner flasks or a bioreactor may be used to generate large numbers of cells.

Robotic automation specifically envisioned for use with the present invention may be obtained from, for example, Tecan (CA, USA). Robotics may include liquid handling tools such as cap-piercing probes and disposable tips to minimize carry-over between samples. In various embodiments, robotics may be utilized in conjunction with one or more bioreactor for culturing cells (e.g., during the maintenance or growth of hESCs, the differentiation of hESCs into hematopoietic cells or endothelial cells, or the differentiation of hematopoietic cells into subsequent lineages such as erythrocytes, etc.).

The approach of the present invention may also be utilized in a single cell assay, using robotic automation, by including the ROCK inhibitors HA100 and H1152 in the medium to improve viability of individualized pluripotent cells. On the robot, the addition of the small molecules HA100 or H1152 to the culture system can, in various embodiments, improve the viability of pluripotent cells. Without the inclusion of these or similar small molecules, survival of pluripotent cells in TeSR is typically low, unless the cells are passed as small clumps or colonies. The ROCK inhibitors allow individualized pluripotent cells to attach to a surface and grow. Thus, the fact that this method works with single ES cells permits the entire process, such as from pluripotent cell proliferation to CD34+ differentiation, to be completely automated in defined conditions.

X. Kits

The present invention also contemplates kits for use in accordance with the present invention. For example, a kit may comprise a differentiation medium described herein in one or more sealed vials. The kit may include a cell, such as a pluripotent stem cell, progenitor cell, hematopoietic progenitor cell, or endothelial progenitor cell.

The kit may also include instructions for producing progenitor cells, such as hematopoietic progenitor cells or endothelial progenitor cells. Alternatively, the instructions may be directed to producing hematopoietic cells, endothelial cells, mast cells, dendritic cells, megakaryocytes, granulocytes, macrophages, or erythrocytes.

Suitable kits include various reagents for use in accordance with the present invention in suitable containers and packaging materials, including tubes, vials, and shrink-wrapped and blow-molded packages.

Materials suitable for inclusion in a kit in accordance with the present invention include, but are not limited to, one or more of the following: a matrix component, fibronectin, collagen, an RGD peptide, BIT 9500, BMP4, VEGF, bFGF, L-glutamine, non-essential amino acids, monothioglycerol, penicillin, streptomycin, an inhibitor of a Rho-associated kinase (ROCK), an inhibitor of myosin II, amino acids, TeSR medium, TeSR2 medium, mTeSR medium, enzymes, trypsin, trypLE, antibiotics, vitamins, salts, minerals, or lipids.

XI. Screening Assays

The invention contemplates screening assays, such as a screening assay useful for identifying a candidate substance for ability to promote differentiation of a pluripotent stem cell into a progenitor cell.

As used herein the term "candidate substance" refers to any substance that affects differentiation of a pluripotent stem cell into a progenitor cell. In certain embodiments, the candidate substance promotes differentiation of a pluripotent stem cell into a progenitor cell. Candidate substances can include fragments or parts of naturally-occurring compounds or may be only found as active combinations of known compounds that are otherwise inactive. In one embodiment, the candidate substances are small molecules. In yet other embodiments, candidate substances may include, but are not limited to, small molecules, peptides or fragments thereof, peptide-like molecules, nucleic acids, polypeptides, peptidomimetics, carbohydrates, lipids, proteins, enzymes, salts, amino acids, vitamins, matrix components, inhibitors, antibiotics, antibodies, antibody fragments, minerals, lipids, or other organic (carbon-containing) or inorganic molecules.

XII. Therapeutic Agents

The present invention further contemplates methods of treating a disease, disorder, or injury by administering to a subject a pharmaceutically effective amount of progenitor cells, hematopoietic cells, or endothelial cells obtained by methods disclosed herein. Administration of these compositions according to the present invention will be via any common route so long as the target tissue is available via that route. This includes administration by systemic or parenteral methods including intravenous injection, intraspinal injection, or intracerebral, intradermal, subcutaneous, intramuscular, or intraperitoneal methods. Depending on the nature of the therapeutic, administration may also be via oral, nasal, buccal, rectal, vaginal or topical means.

Diseases or disorders that may be treated by methods disclosed here include, but are not limited to, a vascular disease or disorder, an immunological disease or disorder, a neuronal disease or disorder, a blood disease or disorder, or an injury. For example, endothelial cells generated by the disclosed methods may be used to produce new blood vessels, which may be used to treat an injury, such as a regional ischemia. Also, hematopoietic progenitor cells produced according to the invention may be differentiated into blood cells to be used in blood transfusions. Alternately, in certain embodiments, hematopoietic cells differentiated according to the invention may be administered to treat a disease such as sickle cell anemia (Hanna et al., 2007).

XIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Defined Differentiation of Human Embryonic Stem Cells to CD34+Hematopoietic Cells At passage 41, human embryonic stem cells were plated onto fibronectin coated plates and cultured in TeSR medium for 7 days. At day 7, the medium was changed from TeSR to CD34 differentiation medium, which is described above as IMDM in Table 1 and includes BIT9500, BMP4, VEGF, bFGF, non-essential amino acids, L-glutamine, Pen-strep, and monothioglycerol.

Cells were maintained in this medium for a total of 10 days, with medium exchanges approximately every other day. At the end of this time CD34+ cells were isolated from the overall population using MACS magnetic sorting technology. The CD34+ cells made up 14% of the overall population, and the sorted cells were over 95% pure.

To ensure that these cells were capable of progressing beyond mere CD34+ status to full-fledged blood differentiation, they were plated into an erythroid differentiation medium.

Fourteen days later, these cells were assayed for expression of glycophorin A, a marker for red blood cells. Approximately 90% of cells assayed expressed glycophorin A at this time, indicating that this method was successful in producing red blood cells.

Additional studies were conducted to assess the capability of this method to produce a broader spectrum of blood cell types. Megakaryocytes were successfully produced using the inventors' established differentiation protocols and granulocyte, macrophage, and red blood cell colonies were produced using the methylcellulose differentiation system, available from Stem Cell Technologies (Vancouver, BC, Canada), and described in Kaufman et al. (2001).

Studies were performed to optimize the amount of time it takes to produce the highest percentage of CD34+ cells. Cells were assayed every other day from day 8 through day 14 in differentiation medium for expression of CD34 and CD43. Expression of both CD34 and CD43 peaked on day 10.

The defined system improved the consistency in the production of CD34+ cells from hESCs, and ~12-14% CD34+ cells were consistently differentiated from human embryonic stem cells over multiple experiments.

This approach allows for the elimination of essentially all or all non-human animal products (i.e., serum, feeder cells, etc.) from this system. Greater possibilities also exist for scalability/automation, as there are no stromal cells, and no complex steps involving embryonic body formation.

Example 2

Defined Differentiation of Individualized Embryonic Cells to CD34+ Hematopoietic Cells Variations in input ES colony size and colony density can lead to substantial variability in performance of any differentiation method. Therefore, the dispersion of ES colonies into individual cells prior to initiating differentiation was investigated. Cultured populations of ES cells were dispersed or individualized with trypsin or TrypLE. Dispersed ES cells were then seeded in TeSR medium, with or without a ROCK inhibitor (H1152, 1 µM). Differentiation procedures described herein were performed with the individualized cultures.

Results

Individualized ES cells plated in TeSR medium on fibronectin-coated surfaces do not attach and survive without the addition of a survival factor such as a ROCK inhibitor (e.g., H1152 at 1 uM). Furthermore, if the seeding density is too low (less than approximately $1 \times 10^4$ cells per $cm^2$), cells detach and lose viability even in the presence of a ROCK inhibitor. If seeded at too high a cell density (greater than $5 \times 10^4$ cells per $cm^2$), cells remain attached, but fail to differentiate into hematoendothelial progenitors. The optimum seeding density between these limits is dependent on the method used for cell expansion, the passage number, and the overall condition of the ES cells.

Time-course studies revealed that the differentiation kinetics differ between cultures where ES cells are plated as individualized cells and cultures where ES cells are plated as colonies with the peak production of hematoendothelial progenitor cells occurring between days 6 and 9 versus days 8 and 12, respectively.

Example 3

Induction of Hematopoietic Differentiation from ES Cells in Low Oxygen or Hypoxic Conditions In an effort to improve the reproducibility and the efficiency of this differentiation method, hypoxic conditions were considered in the generation of hematoendothelial progenitor cells. Hypoxia has been shown to have an important role in vivo in the very early stages of the growing embryo. Before the establishment of the cardiovascular system, mammalian development occurs in a 3% oxygen environment. Studies have indicated that physiological hypoxia may be an important regulator of embryonic angiogenesis and hematopoiesis (Forsythe et al., 1996; Ramirez-Bergeron et al., 2004; Harrison et al., 2002; Cipolleschi et al., 1993).

To test the regulatory effects of low oxygen on hematopoietic progenitor cells at different developmental stages, the protocol for hematopoietic differentiation from pluripotent cells was modified to reflect decreased oxygen levels. A decrease in oxygen concentration to 5% in the cell culture was achieved by the addition of nitrogen gas to the incubator environment, which then consists of 5% $CO_2$, 5% $O_2$, 90% $N_2$. This hypoxic atmosphere promotes an increased differentiation of endothelial and hematopoietic progenitors. In hypoxia a highly viable culture (up to 70% viable cells) analyzed after 6 days of differentiation induction can contain up to 40% hematoendothelial progenitor cells (CD31+) and up to 14% hematopoietic progenitor cells (CD43+). The low oxygen concentration improves hematopoietic differentiation of pluripotent cells independently of the method used to maintain the pluripotent cell culture. This protocol has been tested in hESC maintained in an undifferentiated state using either mouse embryonic fibroblasts as feeder cells or a feeder-independent culture system.

A hypoxic atmosphere might be needed for only the first induction of hematoendothelial differentiation. As it naturally occurs in the adult bone marrow, different stages of hematopoietic development take place in a gradient of oxygen levels, with the hematopoietic progenitor cells occupying the hypoxic niches and the proliferating progenitors distributed along the oxygen gradient. One can therefore envisage the use of a hypoxic atmosphere for the generation of a hematopoietic progenitor cell stage, followed by regular atmospheric oxygen levels in the environment for the further differentiation steps.

Example 4

Defined Differentiation of Stem Cells into Endothelial Cells

Materials and Methods hESCs or iPS cells were seeded at densities between 20,000 and 70,000 cells/cm$^2$ to fibronectin (3-5 μg/cm2) or collagen coated plates. The cells were grown in TeSR1 medium containing the ROCK inhibitor H1152. Cells were placed in a low oxygen incubator (5% oxygen) overnight.

To differentiate the cells, the medium was changed the next day to a medium including the combination of ingredients disclosed in Table 1. After 3 days of culturing, the medium was changed to a medium comprising the combination of ingredients disclosed in Table 1, except that no BMP4 was added to the medium.

After 6 days of differentiation, the cells were magnetically sorted (using MACS) based on the expression of cell surface marker CD31. The CD31+ cells were then plated onto fibronectin (at a concentration of about 0.4 μg/cm2 to 5 μg/cm2) in a medium comprising the ingredients disclosed in Table 1. Alternatively, the bFGF concentration may be decreased to 5 ng/ml. The cells were then expanded and assayed for functionality.

Results

The cells obtained by this method exhibited the molecular and functional characteristics of endothelial cells. For example, the cells expressed CD31, and continued to express CD31 throughout their lifespan. The cells also expressed CD105 (endoglin) and von Willebrand factor (also called Factor VIII). In addition, the cells were capable of taking up acetylated LDL. Functionally, the cells were able to form vascular-like tube structures in a thick layer of matrigel. These results indicate that the methods employed resulted in the production of endothelial cells.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. No. 6,815,450
U.S. Pat. No. 6,943,172
U.S. Pat. No. 7,348,339
U.S. Pat. No. 7,442,548
U.S. Pat. No. 7,459,424
U.S. Application 2006/0084168
U.S. Application 2008/0021035
U.S. Application 2008/0233610
U.S. Application 2009/0004163
U.S. Application 2009/0029462
Bashey et al. *Transfusion*, 47(11):2153-2160, 2007.
Bhardwaj et al., *Nat. Immunol.*, 2:172-180, 2001.
Bhatia et al., *J. Exp. Med.*, 189:1139-1148, 1999.
Chadwick et al., *Blood*, 102(3):906-915, 2003.
Cipolleschi et al., *Blood*, 82:2031-2037, 1993.
Davidson and Zon, *Curr. Top Dev. Biol.*, 50:45-60, 2000.
EP 00187371
Ezashi et al., *Proc. Natl. Acad. Sci. USA* 102(13): 4783-8, 2005.
Fadilah et al., *Stem Cells Dev.*, 16(5):849-856, 2007.
Forsythe et al., *Mol. Cell. Biol.*, 16(9):4604-13, 1996.
Hanna et al., *Science*, 318(5858):1920-1923, 2007.
Harrison et al., *Blood*, 99(1):394, 2002.
Huber et al., *Blood*, 92: 4128-4137, 1998.
Kadaja-Saarepuu et al. *Oncogene*, 27(12):1705-1715, 2008.
Kaufman et al., *Proc. Natl. Acad. Sci. USA*, 98:19, 2001.
Ludwig et al., *Nature Biotech.*, (2):185-187, 2006.
Ludwig et al., *Nature Methods*, 3(8):637-646, 2006.
Marshall et al., *Blood*, 96:1591-1593, 2000.
Nakagawa et al., *Nat. Biotechnol.*, 26(1):101-106, 2008.
PCT Appln. WO 00057913
PCT Appln. WO 00078351
PCT Appln. WO 2006/050330
PCT Appln. WO 98/30679
Ramirez-Bergeron et al., *Development*, 131(18):4623-4634, 2004.
Ratajczak et al., *Br. J. Haematol.*, 93(4):772-782, 1996.
Slukvin et al. In: *Directed Production of Specific Blood Lineages from Human Embryonic Stem Cells*, #33, ASCI/AAP Joint Meet. Posters, 2007.
Takahashi et al. *Cell*, 131(5):861-872, 2007.
Takahashi et al. *Nat. Protoc.*, 2(12):3081-3089, 2007.
Vodyanik et al., *Blood*, 108(6):2095-2105, 2006
Wang et al., *Nature Biotech.*, 25(3):317-318, 2007.
Yamamura et al., *Stem Cells*, 25(1):78-87, 2007.
Yu et al., *Science*, 318(5858):1917-1920, 2007.

What is claimed is:

1. A method for differentiating a human pluripotent stem cell into a CD34+ progenitor cell comprising:
 a) culturing a pluripotent stem cell in a first culture medium that is free or essentially free of feeder cells, the culture comprising a matrix component, wherein said culturing includes
  i) dispersing a pluripotent stem cell colony or clonal cell grouping to form dispersed essentially individual cells, and
  ii) seeding the dispersed cells into the first culture medium at a density of from about 10,000 stem cells per square centimeter of culturing surface to less than 50,000 stem cells per square centimeter of culturing surface; and
 b) differentiating the dispersed cells in a differentiation culture medium comprising at least one recombinant growth factor selected from the group consisting of BMP-4, VEGF, and bFGF, under a hypoxic atmosphere having less than or equal to 5.5% oxygen for a period of time to provide the CD34+ progenitor cells.

2. The method of claim 1, wherein the matrix component comprises fibronectin coated on a culturing surface.

3. The method of claim 1, wherein both step a) and step b) are carried out in a hypoxic atmosphere having less than 5.5% oxygen.

4. A method for differentiating a human pluripotent stem cell into a CD43+ progenitor cell comprising:
 a) culturing a pluripotent stem cell in a first culture medium that is free or essentially free of feeder cells, the culture comprising a matrix component, wherein said culturing includes
  i) dispersing a pluripotent stem cell colony or clonal cell grouping to form dispersed essentially individual cells, and
  ii) seeding the dispersed cells into the first culture medium at a density of from about 10,000 stem cells per square centimeter of culturing surface to less than 50,000 stem cells per square centimeter of culturing surface; and
 b) differentiating the dispersed cells in a differentiation culture medium comprising at least one recombinant growth factor selected from the group consisting of BMP-4, VEGF, and bFGF, under a hypoxic atmosphere having less than or equal to 5.5% oxygen for a period of time to provide the CD43+ progenitor cells.

5. The method of claim 4, wherein the matrix component comprises fibronectin coated on a culturing surface.

6. The method of claim 4, wherein both step a) and step b) are carried out in a hypoxic atmosphere having less than 5.5% oxygen.

7. A method for differentiating a human pluripotent stem cell into a CD31+ progenitor cell comprising:
 a) culturing a pluripotent stem cell in a first culture medium that is free or essentially free of feeder cells, the culture comprising a matrix component, wherein said culturing includes
  i) dispersing a pluripotent stem cell colony or clonal cell grouping to form dispersed essentially individual cells, and
  ii) seeding the dispersed cells into the first culture medium at a density of from about 10,000 stem cells per square centimeter of culturing surface to less than 50,000 stem cells per square centimeter of culturing surface; and
 b) differentiating the dispersed cells in a differentiation culture medium comprising at least one recombinant growth factor selected from the group consisting of BMP-4, VEGF, and bFGF, under a hypoxic atmosphere having less than or equal to 5.5% oxygen for a period of time to provide the CD31+ progenitor cells.

8. The method of claim 7, wherein the matrix component comprises fibronectin coated on a culturing surface.

9. The method of claim 7, wherein both step a) and step b) are carried out in a hypoxic atmosphere having less than 5.5% oxygen.

10. The method of claim 1 or 7, wherein the pluripotent stem cell is an embryonic stem cell or an induced pluripotent stem cell.

11. The method of claim 1 or 7, wherein the hypoxic atmosphere comprises from about 0.5% oxygen gas to about 5.5% oxygen gas.

12. The method of claim 1 or 7, wherein the hypoxic atmosphere comprises from about 1.5% oxygen gas to about 5.3% oxygen gas.

13. The method of claim 1 or 7, wherein the matrix component comprises fibronectin, collagen, or an RGD peptide.

14. The method of claim 1 or 7, wherein the method further comprises harvesting the progenitor cell or its progeny at 8 days to 12 days of culturing.

15. The method of claim 1 or 7, wherein the method further comprises harvesting the progenitor cell or its progeny at 6 days to 9 days of culturing.

16. The method of claim 1 or 7, wherein the differentiation culture medium comprises BMP-4, VEGF, and bFGF.

17. The method of claim 1 or 7, wherein the differentiation culture medium comprises BMP-4 in an amount of from about 5 ng/mL to about 200 ng/mL.

18. The method of claim 1 or 7, wherein the differentiation culture medium comprises VEGF in an amount of from about 5 ng/mL to about 200 ng/mL.

19. The method of claim 1 or 7, wherein the differentiation culture medium comprises bFGF in an amount of from about 5 ng/mL to about 200 ng/mL.

20. The method of claim 1 or 7, wherein the first culture medium and the differentiation culture medium are free or essentially free of serum or feeder cells.

21. The method of claim 1 or 7, wherein the first culture medium comprises TeSR.

22. The method of claim 1 or 7, wherein the first culture medium comprises an inhibitor of a Rho-associated kinase (ROCK).

23. The method of claim 1 or 7, wherein the first culture medium comprises an inhibitor of myosin II.

24. The method of claim 1 or 7, wherein the method further comprises differentiating the progenitor cells into one or more of the group consisting of erythrocytes, macrophages, granulocytes, megakaryocytes, dendritic cells, mast cells, or endothelial cells.

25. The method of claim 24, wherein the further differentiation occurs in culture medium comprising one or more of the group consisting of FMS-like tyrosine kinase 3 ligand (FLT-3ligand), stem cell factor (SCF), thrombopoietin (TPO), interleukin 3 (IL-3), interleukin 6 (IL-6), and heparin.

26. The method of claim 24, wherein the further differentiation occurs in culture medium comprising FMS-like tyrosine kinase 3 ligand (FLT-3 ligand), stem cell factor (SCF), thrombopoietin (TPO), interleukin 3 (IL-3), interleukin 6 (IL-6), and heparin.

27. The method of claim 1 or 7, wherein the differentiation culture medium comprises two or more recombinant growth factors selected from the group consisting of BMP-4, VEGF, and bFGF.

28. The method of claim 1 or 7, wherein the method comprises using a robot to automate at least a portion of the method.

29. The method of claim 1 or 7, wherein a plurality of the pluripotent stem cells are cultured using a bioreactor.

30. The method of claim 1 or 7, further comprising sorting the progenitor cells using magnetic-activated cell sorting (MACS), flow cytometry, or fluorescence-activated cell sorting (FACS).

31. The method of claim 1 or 7, further comprising sorting the progenitor cells based on the expression of one or more of the group consisting of CD34, CD43, and CD31.

32. The method of claim 1 or 7, wherein the pluripotent stem cells are dispersed by treatment with an effective amount of one or more enzymes.

33. The method of claim 32, wherein at least one of the enzymes is trypsin or TrypLE.

34. The method of claim 1 or 7, wherein the differentiation medium is a defined differentiation medium.

35. The method of claim 1 or 7, wherein the differentiation medium further comprises one or more of the group consisting of SCF, TPO, FLT-3 ligand, IL-3, IL-6, and heparin.

36. The method of any one of claim 1, 34 or 7, wherein the human pluripotent stem cell is an induced pluripotent stem cell.

* * * * *

UNITED STATES PATENT AND TRADEMARK OFFICE
CERTIFICATE OF CORRECTION

| | | |
|---|---|---|
| PATENT NO. | : 8,557,580 B2 | Page 1 of 1 |
| APPLICATION NO. | : 12/709764 | |
| DATED | : October 15, 2013 | |
| INVENTOR(S) | : Christine Daigh et al. | |

It is certified that error appears in the above-identified patent and that said Letters Patent is hereby corrected as shown below:

In the Claims

In claim 36, column 29, line 23, delete "34" and insert --4-- therefor.

Signed and Sealed this
Fourth Day of March, 2014

Michelle K. Lee
*Deputy Director of the United States Patent and Trademark Office*